United States Patent [19]
Dartt et al.

[11] Patent Number: 5,869,706
[45] Date of Patent: Feb. 9, 1999

[54] EPOXIDATION PROCESS USING A SYNTHETIC CRYSTALLINE MATERIAL OXIDES OF SILICON AND TITANIUM

[75] Inventors: Christopher B. Dartt; Mark E. Davis, both of Pasadena, Calif.

[73] Assignee: California Institute of Technology, Pasadena, Calif.

[21] Appl. No.: 612,625

[22] Filed: Mar. 6, 1996

Related U.S. Application Data

[60] Provisional application No. 60/009,424 Dec. 27, 1995.
[51] Int. Cl.⁶ ................................................. C07D 301/12
[52] U.S. Cl. ........................... 549/531; 549/523; 502/60; 423/713; 423/704; 423/705; 423/706
[58] Field of Search ..................................... 423/704, 705, 423/706, 713; 502/60, 64; 549/531, 523, 524

[56] References Cited

U.S. PATENT DOCUMENTS

| | | | |
|---|---|---|---|
| 4,410,501 | 10/1983 | Taramaso et al. | 423/326 |
| 4,963,337 | 10/1990 | Zones | 423/277 |
| 5,114,565 | 5/1992 | Zones et al. | 208/138 |
| 5,681,789 | 10/1997 | Saxton et al. | 502/85 |

OTHER PUBLICATIONS

D.R.C. Huybrechts, L. De Bruycker & P.A. Jacobs, "Oxy-functionalization of alkanes with hydrogen peroxide on titanium silicalite", *Nature*, vol. 345, 17 May 1990, pp. 240–242.

T. Tatsumi, M. Nakamura, S. Negishi & H. Tominaga, "Shape–selective Oxidation of Alkanes with $H_2O_2$ catalysed by Titanosilicate", *J. Chem. Soc., Chem. Commun.*, 1990, pp. 476–477. (no month).

M.S. Rigutto, R. de Ruiter, J.P.M. Niederer & H. van Bekkum, "Titanium–Containing Large Pore Molecular Sieves from Boron–Beta: Preparation, Characterization and Catalysis", *Studies in Surface Science and Catalysis,* vol. 84, 1994, pp. 2245–2253. (no month).

*Primary Examiner*—Michael Lewis
*Assistant Examiner*—Thomas G. Dunn, Jr.
*Attorney, Agent, or Firm*—Richard J. Sheridan

[57] ABSTRACT

Zeolite SSZ-33 containing titanium in its framework is prepared by post-synthesis treatment with titanium tetrachloride. The titanium-containing SSZ-33 is useful as a catalyst in oxidation reactions.

13 Claims, No Drawings

EPOXIDATION PROCESS USING A SYNTHETIC CRYSTALLINE MATERIAL OXIDES OF SILICON AND TITANIUM

This application claims the benefit of U.S. Provisional Application No. 60/009,424, filed Dec. 27, 1995 now abandoned.

BACKGROUND OF THE INVENTION

The partial oxidation of low value hydrocarbons such as alkanes and alkenes into high value products such as alcohols and epoxides is of great commercial interest. These oxidation products are not only valuable as is, but also as intermediates for specialty chemicals including pharmaceuticals and pesticides.

U.S. Pat. No. 4,410,501, issued Oct. 18, 1983 to Esposito et al., discloses a titanium-containing analogue of the all-silica ZSM-5 molecular sieve. This material (known as "TS-1") has been found to be useful in catalyzing a wide range of partial oxidation chemistries, for example the production of catechol and hydroquinone from phenol and hydrogen peroxide ($H_2O_2$) and the manufacture of propylene oxide and cyclohexanone oxime from propylene and cyclohexanone, respectively. In addition, TS-1 can be used to catalyze the reaction of alkanes and aqueous $H_2O_2$ to form alcohols and ketones. (See Huybrechts, D. R. C. et al., *Nature* 1990, 345, 240–242 and Tatsumi, T. et al., *J.C.S. Chem. Commun.* 1990, 476–477.)

TS-1 has many salient features, other than its catalytic abilities, which make it attractive as a commercial catalyst. Most importantly, it is a solid. This allows for easy separation from the reactants and products (typically liquids) by simple, inexpensive filtration. Moreover, this solid has high thermal stability and a very long lifetime.

Calcination in air at moderate temperatures (550° C.) restores the material to its original catalytic ability. TS-1 performs best at mild temperatures (<100° C.) and pressures (1 atm). The oxidant used for reactions catalyzed by TS-1 is aqueous $H_2O_2$, which is important because aqueous $H_2O_2$ is relatively inexpensive and its by-product is water. Hence, the choice of oxidant is favorable from both a commercial and environmental point of view.

While a catalyst system based on TS-1 has many useful features, it has one serious drawback. The zeolite structure of TS-1 includes a regular system of pores which are formed by nearly circular rings of ten silicon atoms (called 10-membered rings, or simply "10 rings") creating pore diameters of approximately 5.5 Å. This small size results in the exclusion of molecules larger than 5.5 Å. Because the catalytically active sites are located within the pores of the zeolite, any exclusion of molecules from the pores results in poor catalytic activity.

U.S. Pat. No. 4,963,337, Oct. 16, 1990 to Zones, discloses the boron-containing zeolite designated therein "SSZ-33". This zeolite has some of its pores formed by 10-membered rings and others by 12-membered rings. This allows for larger molecules, which would be excluded from the pores of TS-1, to enter the pore system of SSZ-33.

It has now been discovered that when SSZ-33 is modified by replacing at least part of the framework boron atoms with titanium atoms, a catalyst results (designated herein as "Ti-SSZ-33") which has all the benefits of TS-1 without the drawback of its smaller pore system. In direct contrast to TS-1, in which the zeolite is synthesized in the presence of titanium, the aforementioned modification of SSZ-33 to Ti-SSZ-33 involves post-synthesis treatment of as-made samples of SSZ-33 to substitute titanium atoms for at least part of the boron atoms in the as-made SSZ-33.

A post-synthetic treatment of this type is described in Rigutto et al., *Studies in Surface Science and Catalysis,* 1994, 84c, 2245–2252 wherein the incorporation of titanium into boron-containing zeolite beta is disclosed. There, the post-synthesis treatment involved treatment of the boron-containing zeolite beta with titanium tetrachloride ($TiCl_4$) followed by treatment with methanol.

While zeolite beta has a larger pore system than either TS-1 or SSZ-33, it is less thermally stable than those zeolites. Thus, there exists a need for a titanium-containing zeolite which has both relatively large pores and acceptable thermal stability. The zeolite of this invention, Ti-SSZ-33, satisfies that need.

SUMMARY OF THE INVENTION

The present invention provides a zeolite having a mole ratio of an oxide selected from the group consisting of silicon oxide, germanium oxide, and mixtures thereof to an oxide selected from the group consisting of titanium oxide and mixtures of titanium oxide with boron oxide, said mole ratio being greater than about 20:1, wherein the elemental mole ratio of titanium to silicon, germanium or mixture thereof is at least about 0.005, and the zeolite has the X-ray diffraction lines of Table I.

The present invention further provides a method of preparing a zeolite having a mole ratio of an oxide selected from the group consisting of silicon oxide, germanium oxide, and mixtures thereof to an oxide selected from the group consisting of titanium oxide and mixtures of titanium oxide with boron oxide, said mole ratio being greater than about 20:1, wherein the elemental mole ratio of titanium to silicon, germanium or mixture thereof is at least about 0.005, and the zeolite has the X-ray diffraction lines of Table I, said method comprising:

A. preparing an aqueous mixture containing sources of (1) a tricyclodecane quaternary ammonium ion, (2) boron oxide, (3) an oxide selected from silicon oxide, germanium oxide and mixtures thereof and (4) an alkali metal oxide;

B. maintaining the mixture at a temperature of at least 140° C. until crystals of the zeolite form;

C. recovering the zeolite crystals;

D. contacting the zeolite crystals with titanium tetrachloride vapor; and

E. contacting the product of step D with a $C_1$ to $C_3$ alcohol vapor.

Also provided by the present invention is a catalytic oxidation process comprising contacting under oxidation conditions (1) a reactant which is catalytically oxidizable in the presence of hydrogen peroxide, (2) aqueous hydrogen peroxide and (3) a catalytically effective amount of an oxidation catalyst comprising a zeolite having a mole ratio of an oxide selected from the group consisting of silicon oxide, germanium oxide, and mixtures thereof to an oxide selected from the group consisting of titanium oxide and mixtures of titanium oxide with boron oxide, said mole ratio being greater than about 20:1, wherein the elemental mole ratio of titanium to silicon, germanium or mixture thereof is at least about 0.005, and the zeolite has the X-ray diffraction lines of Table I. The present invention also includes such an oxidation process wherein the oxidizable reactant is a hydrocarbon.

Further provided in accordance with this invention is a process for the epoxidation of an olefin comprising contacting said olefin with hydrogen peroxide in the presence of a catalytically effective amount of a catalyst comprising a zeolite having a mole ratio of an oxide selected from silicon oxide, germanium oxide, and mixtures thereof to an oxide selected from titanium oxide and mixtures of titanium oxide with boron oxide, greater than about 20:1, wherein the elemental mole ratio of titanium to silicon, germanium or mixture thereof is at least about 0.005, and wherein the zeolite has the X-ray diffraction lines of Table I.

DETAILED DESCRIPTION OF THE INVENTION

SSZ-33 zeolites can be suitably prepared as described in U.S. Pat. No. 4,963,337, issued Oct. 16, 1990 to Zones, which is incorporated by reference herein in its entirety. Thus, SSZ-33 can be prepared from an aqueous solution containing sources of an alkali metal oxide, a tricyclodecane quaternary ammonium ion, boron oxide, and an oxide of silicon or germanium, or mixture of the two. The reaction mixture should have a composition in terms of mole ratios falling within the following ranges:

|  | Broad | Preferred |
|---|---|---|
| $YO_2/W_2O_3$ | 20–200 | 30–60 |
| $OH^-/YO_2$ | 0.10–1.0 | 0.20–0.30 |
| $Q/YO_2$ | 0.05–0.50 | 0.10–0.25 |
| $M^+/YO_2$ | 0.05–0.30 | 0.05–0.15 |
| $H_2O/YO_2$ | 15–300 | 25–60 |
| $Q/Q + M^+$ | 0.30–0.70 | 0.40–0.60 | wherein Q is a tricyclodecane quaternary ammonium ion, Y is silicon, germanium or both, and W is boron. M is an alkali metal, preferably sodium. The organic compound which acts as a source of the quaternary ammonium ion employed can provide hydroxide ion.

The tricyclodecane quaternary ammonium ion component Q, of the crystallization mixture, is derived from the quaternary ammonium compound. Preferably, the tricyclodecane quaternary ammonium ion is derived from a tricyclo [5.2.1.0$^{2,6}$]decane compound of the formula:

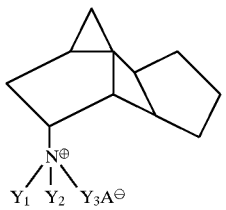

wherein each of $Y_1$, $Y_2$, and $Y_3$ independently is a lower alkyl and most preferably methyl; and $A^-$ is an anion which is not detrimental to the formation of the zeolite.

By "lower alkyl" is meant alkyl of from about 1 to 3 carbon atoms. Representative anions include halides (such as fluoride, chloride, bromide and iodide), hydroxide, acetate, sulfate, and carboxylate. Hydroxide is the most preferred anion. It may be beneficial to ion exchange, for example, the halide for hydroxide ion, thereby reducing or eliminating the alkali metal hydroxide quantity required.

The reaction mixture is prepared using standard zeolitic preparation techniques. Sources of boron for the reaction mixture include borosilicate glasses and other reactive boron oxides. These include borates, boric acid and borate esters. Typical sources of silicon oxide include fumed silica, silicates, silica hydrogel, silicic acid, colloidal silica, tetraalkyl orthosilicates, and silica hydroxides.

The reaction mixture is maintained at an elevated temperature until the crystals of the zeolite are formed. The temperatures during the hydrothermal crystallization step are typically maintained from about 140° C. to about 200° C., preferably from about 150° C. to about 170° C. and most preferably from about 155° C. to about 165° C. The crystallization period is typically greater than 1 day and preferably from about 3 days to about 7 days.

The hydrothermal crystallization is conducted under pressure and usually in an autoclave so that the reaction mixture is subject to autogenous pressure. The reaction mixture can be stirred during crystallization.

Once the zeolite crystals have formed, the solid product is separated from the reaction mixture by standard mechanical separation techniques such as filtration. The crystals may be water-washed and then dried, e.g., at 90° C. to 150° C. from 8 to 24 hours, to obtain the as synthesized, SSZ-33 zeolite crystals. The drying step can be performed at atmospheric or subatmospheric pressures.

During the hydrothermal crystallization step, the SSZ-33 crystals can be allowed to nucleate spontaneously from the reaction mixture. The reaction mixture can also be seeded with SSZ-33 crystals both to direct, and accelerate the crystallization, as well as to minimize the formation of undesired borosilicate contaminants.

SSZ-33 zeolites preferably have a $YO_2:W_2O_3$ mole ratio greater than about 20:1 and can be made essentially alumina free. As prepared, the $YO_2:W_2O_3$ mole ratio is typically in the range of 20:1 to about 100:1. Higher mole ratios can be obtained by treating the zeolite with chelating agents or acids to extract boron from the zeolite lattice. The silica-:boron oxide mole ratio can also be increased by using silicon and carbon halides and other similar compounds.

Once the SSZ-33 has been synthesized, it is subjected to the post-synthesis treatment described in Rigutto et al., *Studies in Surface Science and Catalysis*, 1994, 84c, 2245–2252, which is incorporated herein by reference in its entirety, to incorporate titanium atoms into the framework of the SSZ-33. This treatment involves reacting the SSZ-33 (predried at 400° C.) at 300° C. in a flow of dry inert gas (e.g., nitrogen or argon) saturated with $TiCl_4$ vapor at room temperature. The resulting product is then cooled to about 80° C. in an inert atmosphere and contacted with a flow of alcohol vapor, followed by calcination at 300° C. in dry air and a final hot alcohol wash to remove residual extra-framework boron. The alcohol may be a $C_1$ to $C_3$ alcohol, with methanol being the preferred alcohol. If a $C_3$ alcohol is used, it is preferred that it be isopropanol. The resulting product is Ti-SSZ-33 having titanium atoms in the zeolite framework.

Ti-SSZ-33 as synthesized (i.e., after treatment with $TiCl_4$) has a mole ratio of an oxide selected from the group consisting of silicon oxide, germanium oxide, and mixtures thereof to an oxide selected from the group consisting of titanium oxide and mixtures of titanium oxide with boron oxide, said mole ratio being greater than about 20:1, wherein the elemental mole ratio of titanium to silicon, germanium or mixture thereof is at least about 0.005. Ti-SSZ-33 further has a composition, in terms of elemental mole ratios, shown in Table A below. It should be understood that "Si" in Table A refers to silicon, germanium and mixtures of silicon and germanium.

TABLE A

As-Synthesized Ti-SSZ-33 Composition

| Broad | Preferred |
|---|---|
| 0.005 < Ti/Si < 0.2 | 0.01 < Ti/Si < 0.05 |
| 0 < B/Si < 0.01 | B/Si = 0 |

Ti-SSZ-33 zeolites, as synthesized, have a crystalline structure whose X-ray powder diffraction pattern shows the following characteristic lines:

TABLE I

AS-SYNTHESIZED Ti-SSZ-33

| 2 θ | d/n | Rel. Intensity[a] |
|---|---|---|
| 7.86 | 11.25 | VS |
| 20.48 | 4.336 | VS |
| 21.47 | 4.139 | M–S |
| 22.03 | 4.035 | VS |
| 23.18 | 3.837 | VS |
| 26.83 | 3.323 | M–S |

[a]The X-ray patterns provided are based on a relative intensity scale in which the strongest line in the X-ray pattern is assigned a value of 100: W (weak) is less than 20; M (medium) is between 20 and 40; S (strong) is between 40 and 60; VS (very strong) is greater than 60.

The actual intensities of the diffraction lines in Table I are indicated below in Table IA. The relative intensities are shown in Table IA as $100 \times I/I_o$, where $I_o$ is the intensity of the strongest line or peak.

TABLE IA

AS-SYNTHESIZED Ti-SSZ-33

| 2 θ | d/n | 100 × I/I$_o$ |
|---|---|---|
| 7.86 | 11.25 | 90 |
| 20.48 | 4.336 | 100 |
| 21.47 | 4.139 | 40 |
| 22.03 | 4.035 | 90 |
| 23.18 | 3.837 | 64 |
| 26.83 | 3.323 | 40 |

The X-ray powder diffraction patterns were determined using a Scintag XDS-2000 diffractometer equipped with a liquid nitrogen cooled germanium detector using Cu—Kα radiation. Fluorophologopite mica (Standard Reference Material 675, National Bureau of Standards) was used as an external standard for all samples. Data were collected with a step size of 0.02 degrees and a step time of ten seconds.

The X-ray diffraction pattern of Table I is characteristic of Ti-SSZ-33 zeolites. The zeolite produced by exchanging the metal or other cations present in the zeolite with various other cations yields substantially the same diffraction pattern although there can be minor shifts in interplanar spacing and minor variations in relative intensity. Minor variations in the diffraction pattern can also result from variations in the organic compound used in the preparation and from variations in the silica-to-boron mole ratio from sample to sample. Calcination can also cause minor shifts in the X-ray diffraction pattern. Notwithstanding these minor perturbations, the basic crystal lattice structure remains unchanged.

After calcination, the Ti-SSZ-33 zeolites have a crystalline structure whose X-ray powder diffraction pattern shows the characteristic lines as indicated in Table II below.

TABLE II

CALCINED Ti-SSZ-33

| 2 θ | d/n | Rel. Intensity |
|---|---|---|
| 7.81 | 11.32 | VS |
| 20.43 | 4.347 | S |
| 21.44 | 4.144 | W |
| 22.02 | 4.037 | M–S |
| 23.18 | 3.837 | M |
| 26.80 | 3.326 | M |

The actual intensities of the diffraction lines in Table II are indicated below in Table IIA. The relative intensities are shown in Table IIA as $100 \times I/I_o$, where $I_o$ is the intensity of the strongest line or peak.

TABLE IIA

CALCINED Ti-SSZ-33

| 2 θ | d/n | 100 × I/I$_o$ |
|---|---|---|
| 7.81 | 11.32 | 100 |
| 20.43 | 4.347 | 46 |
| 21.44 | 4.144 | 9 |
| 22.02 | 4.037 | 41 |
| 23.18 | 3.837 | 28 |
| 26.80 | 3.326 | 31 |

Usually, it is desirable to remove any alkali metal cation by ion exchange and replace it with hydrogen, ammonium, or any desired metal ion. The zeolite can be leached with chelating agents, e.g., EDTA or dilute acid solutions, to increase the silica:boron mole ratio. The zeolite can also be steamed; steaming helps stabilize the crystalline lattice to attack from acids.

The Ti-SSZ-33 prepared by the process of this invention is useful as a catalyst in oxidation reactions, particularly in the oxidation of hydrocarbons. Examples of such reactions include, but are not limited to, the epoxidation of olefins, the oxidation of alkanes, and the oxidation of sulfur-containing, nitrogen-containing or phosphorus-containing compounds.

The amount of Ti-SSZ-33 catalyst employed is not critical, but should be sufficient so as to substantially accomplish the desired oxidation reaction in a practicably short period of time (i.e., a catalytically effective amount). The optimum quantity of catalyst will depend upon a number of factors including reaction temperature, the reactivity and concentration of the substrate, hydrogen peroxide concentration, type and concentration of organic solvent, as well as the activity of the catalyst. Typically, however, the amount of catalyst will be from about 0.001 to 10 grams per mole of substrate.

Typically, the titanium-containing crystalline zeolites of this invention are thermally treated (calcined) prior to use as a catalyst.

The catalyst may be utilized in powder, pellet, microspheric, monolithic, extruded, or any other suitable physical form. The use of a binder (co-gel) or support in combination with the Ti-SSZ-33 may be advantageous. Supported or bound catalysts may be prepared by the methods known in the art to be effective for zeolite catalysts in general.

Illustrative binders and supports (which preferably are non-acidic in nature) include silica, alumina, silica-alumina, silica-titania, silica-thoria, silica-magnesia, silica-zirconia, silica-beryllia, and ternary compositions of silica with other refractory oxides. Also useful are clays such as montmorillonites, kaolins, bentonites, halloysites, dickites, nacrites and anaxites. The proportion of Ti-SSZ-33 to binder may range from about 99:1 to about 1:99, but preferably is from about 5:95 to about 80:20, all expressed on a weight basis.

The oxidizing agent employed in the oxidation processes of this invention is a hydrogen peroxide source such as hydrogen peroxide ($H_2O_2$) or a hydrogen peroxide precursor (i.e., a compound which under the oxidation reaction conditions is capable of generating or liberating hydrogen peroxide).

The amount of hydrogen peroxide relative to the amount of substrate is not critical, but must be sufficient to cause oxidation of at least some of the substrate. Typically, the molar ratio of hydrogen peroxide to substrate is from about 100:1 to about 1:100, preferably 10:1 to about 1:10. When the substrate is an olefin containing more than one carbon—carbon double bond, additional hydrogen peroxide may be required. Theoretically, one equivalent of hydrogen peroxide is required to oxidize one equivalent of a mono-unsaturated substrate, but it may be desirable to employ an excess of one reactant to optimize selectivity to the epoxide. In particular, the use of a moderate to large excess (e.g., 50 to 200%) of olefin relative to hydrogen peroxide may be advantageous for certain substrates.

If desired, a solvent may additionally be present during the oxidation reaction in order to dissolve the reactants other than the Ti-SSZ-33, to provide better temperature control, or to favorably influence the oxidation rates and selectivities. The solvent, if present, may comprise from 1 to 99 weight percent of the total oxidation reaction mixture and is preferably selected such that it is a liquid at the oxidation reaction temperature. Organic compounds having boiling points at atmospheric pressure of from about 50° C. to about 150° C. are generally preferred for use. Excess hydrocarbon may serve as a solvent or diluent. Illustrative examples of other suitable solvents include, but are not limited to, ketones (e.g., acetone, methyl ethyl ketone, acetophenone), ethers (e.g., tetrahydrofuran, butyl ether), nitriles (e.g., acetonitrile), aliphatic and aromatic hydrocarbons, halogenated hydrocarbons, and alcohols (e.g., methanol, ethanol, isopropyl alcohol, t-butyl alcohol, alpha-methyl benzyl alcohol, cyclohexanol). More than one type of solvent may be utilized. Water may also be employed as a solvent or diluent.

The reaction temperature is not critical, but should be sufficient to accomplish substantial conversion of the substrate within a reasonably short period of time. It is generally advantageous to carry out the reaction to achieve as high a hydrogen peroxide conversion as possible, preferably at least about 50%, more preferably at least about 90%, most preferably at least about 95%, consistent with reasonable selectivities. The optimum reaction temperature will be influenced by catalyst activity, substrate reactivity, reactant concentrations, and type of solvent employed, among other factors, but typically will be in a range of from about 0° C. to about 150° C. (more preferably from about 25° C. to about 120° C.). Reaction or residence times from about one minute to about 48 hours (more desirably from about ten minutes to about eight hours) will typically be appropriate, depending upon the above-identified variables. Although subatmospheric pressures can be employed, the reaction is preferably performed at atmospheric or at elevated pressure (typically, between one and 100 atmospheres), especially when the boiling point of the substrate is below the oxidation reaction temperature. Generally, it is desirable to pressurize the reaction vessel sufficiently to maintain the reaction components as a liquid phase mixture. Most (over 50%) of the substrate should preferably be present in the liquid phase.

The oxidation process of this invention may be carried out in a batch, continuous, or semi-continuous manner using any appropriate type of reaction vessel or apparatus such as a fixed bed, transport bed, fluidized bed, stirred slurry, or CSTR reactor. The reactants may be combined all at once or sequentially. For example, the hydrogen peroxide or hydrogen peroxide precursor may be added incrementally to the reaction zone. The hydrogen peroxide could also be generated in situ within the same reactor zone where oxidation is taking place.

Once the oxidation has been carried out to the desired degree of conversion, the oxidized product may be separated and recovered from the reaction mixture using any appropriate technique such as fractional distillation, extractive distillation, liquid-liquid extraction, crystallization, or the like.

Olefin Epoxidation

One of the oxidation reactions for which Ti-SSZ-33 is useful as a catalyst is the epoxidation of olefins. The olefin substrate epoxidized in the process of this invention may be any organic compound having at least one ethylenically unsaturated functional group (i.e., a carbon—carbon double bond) and may be a cyclic, branched or straight-chain olefin. The olefin may contain aryl groups (e.g., phenyl, naphthyl). Preferably, the olefin is aliphatic in character and contains from 2 to about 20 carbon atoms. The use of light (low-boiling) $C_2$ to $C_{10}$ mono-olefins is especially advantageous.

More than one carbon—carbon double bond may be present in the olefin, i.e., dienes, trienes and other polyunsaturated substrates may be used. The double bond may be in a terminal or internal position in the olefin or may alternatively form part of a cyclic structure (as in cyclooctene, for example).

Other examples of suitable substrates include unsaturated fatty acids or fatty acid derivatives such as esters.

The olefin may contain substituents other than hydrocarbon substituents such as halide, carboxylic acid, ether, hydroxy, thiol, nitro, cyano, ketone, acyl, ester, anhydride, amino, and the like.

Exemplary olefins suitable for use in the process of this invention include ethylene, propylene, the butenes (i.e., 1,2-butene, 2,3-butene, isobutylene), butadiene, the pentenes, isoprene, 1-hexene, 3-hexene, 1-heptene, 1-octene, diisobutylene, 1-nonene, 1-tetradecene, pentamyrcene, camphene, 1-undecene, 1-dodecene, 1-tridecene, 1-tetradecene, 1-pentadecene, 1-hexadecene, 1-heptadecene, 1-octadecene, 1-nonadecene, 1-eicosene, the trimers and tetramers of propylene, cyclopentene, cyclohexene, cycloheptene, cyclooctene, cyclooctadiene, dicyclopentadiene, methylenecyclopropane, methylenecyclopentane, methylenecyclohexane, vinyl cyclohexane, vinyl cyclohexene, methallyl ketone, allyl chloride, the dichlorobutenes, allyl alcohol, allyl carbonate, allyl acetate, alkyl acrylates and methacrylates, diallyl maleate, diallyl phthalate, and unsaturated fatty acids, such as oleic acid, linolenic acid, linoleic acid, erucic acid, palmitoleic acid, and ricinoleic acid and their esters (including mono-, di-, and triglyceride esters) and the like.

Olefins which are especially useful for epoxidation are the $C_2$–$C_{20}$ olefins having the general structure $$R^3R^4C=CR^5R^6$$

wherein $R^3$, $R^4$, $R^5$ and $R^6$ are the same or different and are selected from the group consisting of hydrogen and $C_1$–$C_{18}$ alkyl.

Mixtures of olefins may be epoxidized and the resulting mixtures of epoxides either employed in the mixed form or separated into the different component epoxides.

The following examples illustrate but do not limit the present invention.

EXAMPLES

Example 1

Preparation of Zeolite SSZ-33

Three samples of SSZ-33 were synthesized using the organic template N,N,N-trimethyltricyclo[5.2.1.0$^{2,6}$]decane ammonium hydroxide. The reactive gels had the following molar composition:

$$SiO_2:xB_2O_3:0.2Q:0.1NaOH:40H_2O$$

where Q represents the organic template.

A typical synthesis involved the addition of 0.363 g of 50 wt % aqueous sodium hydroxide to 0.139 g boric acid dissolved in 17.47 g of a 11 wt % aqueous solution of the template. 16.71 Grams of deionized water was then added and the mixture was stirred until the solution was homogeneous. 2.7 Grams of fumed silica (Cab-O-Sil M5) was then added under agitation and the mixture was allowed to stir for one hour. The resulting gel was then transferred to a Teflon-lined autoclave and heated to 160° C. for ten days under rotation (40 RPM). The resulting crystalline solid was then recovered by filtration and washed with water. After allowing the solid to dry overnight at 100° C., it was calcined to 590° C. for four hours in air to remove occluded organic material.

The three samples of SSZ-33 were prepared using the above-described gel composition where x=0.0125, 0.0175 and 0.025, and were designated SSZ-33 (1), SSZ-33 (2) and SSZ-33 (3), respectively.

The XRD patterns of samples SSZ-33 (1–3) revealed no peaks attributable to impurities. As shown in Table C below, the boron content of the SSZ-33 samples increased with increasing boron concentration in the synthesis gel.

In an attempt to prepare titanium-containing SSZ-33 with low titanium content, the SSZ-33 samples were synthesized with small boron contents. In addition, these samples were used in the calcined form without modification. Because sodium is present in the synthesis gels of SSZ-33, the samples contained some Na$^+$. Therefore, boron sites were balanced by Na$^+$ and protons. The data in Table C show that the sodium content in the SSZ-33 samples increased with lower boron incorporation.

TABLE C

| Sample | B/Si in solid, (gel) | Na/B | Unit Cell Volume |
|---|---|---|---|
| SSZ-33(1) | 0.031, (0.025) | 0.46 | 3474.0 |
| SSZ-33(2) | 0.035, (0.035) | 0.24 | 3460.2 |
| SSZ-33(3) | 0.044, (0.050) | 0.19 | 3456.5 |

Example 2

Preparation of Ti-SSZ-33

SSZ-33 (1–3) were subjected to post-synthetic treatment to incorporate titanium atoms into their frameworks. A typical post-synthetic treatment involved loading 300 mg of calcined SSZ-33 into a quartz reactor and heating to 300° C. in a flow of dry argon to dehydrate the SSZ-33. The dehydrated sample (still at 300° C.) was then exposed to a flow (40 ml/min.) of argon bubbled through a vessel containing TiCl$_4$ (Aldrich, used as received) maintained at 22° C. The TiCl$_4$ flow was continued for about one hour. The sample was then cooled to 100° C. and the argon stream was redirected through another bubbler containing methanol at room temperature. This methanol treatment was conducted for 12 hours. The flow was then switched to dry air, and the sample was calcined at 400° C. As a final precaution to remove any extra-framework boron, the sample was removed from the quartz reactor and refluxed in methanol for one hour and recovered by filtration. A final calcination at 590° C. was performed.

The resulting products, designated Ti-SSZ-33 (1–3), had unit cell volumes of 3515.8, 3519.0 and 3527.9, respectively. This expansion of the unit cell volume indicates that Ti-SSZ-33 (1–3) contain framework titanium.

Comparative Example A

Preparation of TS-1

0.41 Gram of tetraethylorthotitanate (TEOT) were added to 12.29 g of tetraethylorthosilicate (TEOS). In a separate beaker, 24.00 g of water were added to 13.20 g of a 40% aqueous tetrapropylammonium hydroxide solution. The aqueous solution was added dropwise to the silica/titania solution under vigorous stirring. The combined mixture was then stirred at room temperature for 10 hours to allow the alcohols formed from the hydrolysis reaction to evaporate. The synthesis mixture was then transferred to a Teflon-lined autoclave. After five days at 175° C. under slow rotation, the autoclave was quickly cooled to room temperature and its contents were centrifuged to separate the resulting white solid from the mother liquor. The product was washed several times with water and dried in air. Calcination in air at 550° C. for several hours removed all occluded organic material allowing the sample to be used for catalytic testing.

The solid produced by the above procedure was determined by analysis to be TS-1 with a Si/Ti mole ratio of 53.

Example 3

Catalytic Epoxidation of Olefins

The catalysts shown in Table D below were tested for catalytic activity. A typical test was performed in a 25 ml glass reactor immersed in a constant temperature oil bath and used 30% hydrogen peroxide as the oxidant. The 1-hexene reactions were carried out in methanol for two hours at 50° C. with vigorous stirring. Each reaction utilized 50 mg of catalyst, 6.0 g solvent, 8.25 mmol 1-hexene and 2.08 mmol H$_2$O$_2$. The cyclohexene and cyclooctene reactions were performed in methanol for three hours at 70° C. with vigorous stirring. Each reaction utilized 50 mg catalyst, 6.0 g methanol, 9 mmol olefin and 3 mmol H$_2$O$_2$. The results from each catalyst are shown in Table D below.

TABLE D

| Sample | Ti/Si | 1-Hexene Conversion (%) | Epoxide Selectivity (%) | H$_2$O$_2$ Efficiency (%) |
|---|---|---|---|---|
| TS-1 | 0.019 | 11.9 | 97 | 98 |
| Ti-SSZ-33(1) | 0.039 | 4.0 | 12 | 74 |
| Ti-SSZ- | 0.044 | 5.1 | 44 | 49 |

TABLE D-continued

| Sample | Ti/Si | | | |
|---|---|---|---|---|
| 33(2) Ti-SSZ-33(3) | 0.047 | 5.7 | 27 | 49 |

| Sample | Ti/Si | Cyclohexene Conversion (%) | Epoxide Selectivity (%) | H₂O₂ Efficiency (%) |
|---|---|---|---|---|
| TS-1 | 0.019 | 2.4 | 36 | 100 |
| Ti-SSZ-33(1) | 0.039 | 21.4 | 0 | 96 |
| Ti-SSZ-33(2) | 0.044 | 23.3 | 2 | 89 |
| Ti-SSZ-33(3) | 0.047 | 25.5 | 1 | 93 |

| Sample | Ti/Si | Cyclooctene Conversion (%) | Epoxide Selectivity (%) | H₂O₂ Efficiency (%) |
|---|---|---|---|---|
| TS-1 | 0.019 | 2.0 | 100 | 98 |
| Ti-SSZ-33(1) | 0.039 | 13.7 | 95 | 84 |
| Ti-SSZ-33(2) | 0.044 | 24.2 | 99 | 86 |
| Ti-SSZ-33(3) | 0.047 | 25.3 | 99 | 91 |

In Table D, the $H_2O_2$ efficiency is simply the ratio of moles of epoxide formed over the moles of $H_2O_2$ reacted.

The results in Table D demonstrate that TS-1 converts the smaller molecule, 1-hexene. However, for the much larger molecule, cyclooctene, the conversion using Ti-SSZ-33 is considerably higher than when TS-1 was used as the catalyst. This shows that the larger pore system of Ti-SSZ-33 gives a distinct advantage over TS-1 for the epoxidation of larger molecules. The catalytic activity of Ti-SSZ-33 in this reaction is also an indicator that the Ti-SSZ-33 contains titanium in its framework.

What is claimed is:

1. A zeolite having a mole ratio, of an oxide selected from silicon oxide, germanium oxide, and mixtures thereof to an oxide selected from titanium oxide and mixtures of titanium oxide with boron oxide, greater than about 20:1, and wherein the elemental mole ratio of titanium to silicon, germanium or mixture thereof is at least about 0.005 and having the X-ray diffraction lines of Table I.

2. The zeolite of claim 1 wherein the elemental mole ratio of titanium to silicon, germanium or mixture thereof is about 0.005 to about 0.2.

3. The zeolite of claim 1 wherein the elemental mole ratio of titanium to silicon, germanium or mixture thereof is about 0.01 to about 0.05.

4. A method of preparing a zeolite having a mole ratio of an oxide selected from silicon oxide, germanium oxide, and mixtures thereof to an oxide selected from titanium oxide and mixtures of titanium oxide with boron oxide, greater than about 20:1, and wherein the elemental mole ratio of titanium to silicon, germanium or mixture thereof is at least about 0.005, and having the X-ray diffraction lines of Table I, said method comprising:

A. preparing an aqueous mixture containing sources of (1) a tricyclodecane quaternary ammonium ion, (2) boron oxide (3) an oxide selected from silicon oxide, germanium oxide and mixtures thereof, and (4) an alkali metal oxide;

B. maintaining the mixture at a temperature of at least 140° C. until crystals of the zeolite form;

C. recovering the zeolite crystals;

D. calcining the zeolite crystals to remove occluded organic material;

E. contacting the zeolite crystals with titanium tetrachloride vapor; and

F. contacting the product of step E with a $C_1$ to $C_3$ alcohol vapor.

5. The method of claim 4 wherein the tricyclodecane quaternary ammonium ion has the formula:

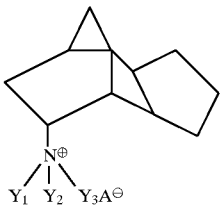

wherein each of $Y_1$, $Y_2$ and $Y_3$ independently is a lower alkyl.

6. The method of claim 4 wherein the alcohol is methanol.

7. A catalytic oxidation process comprising contacting under oxidation conditions (1) a reactant which is catalytically oxidizable in the presence of hydrogen peroxide, (2) aqueous hydrogen peroxide and (3) a catalytically effective amount of an oxidation catalyst comprising a zeolite having a mole ratio of an oxide selected from the group consisting of silicon oxide, germanium oxide, and mixtures thereof to an oxide selected from the group consisting of titanium oxide and mixtures of titanium oxide with boron oxide, said mole ratio being greater than about 20:1, wherein the elemental mole ratio of titanium to silicon, germanium or mixture thereof is at least about 0.005, and the zeolite has the X-ray diffraction lines of Table I.

8. The process of claim 7 wherein the elemental mole ratio of titanium to silicon, germanium or mixture thereof is about 0.005 to about 0.2.

9. The process of claim 7 wherein the elemental mole ratio of titanium to silicon, germanium or mixture thereof is about 0.01 to about 0.05.

10. The process of claim 7 wherein the oxidizable reactant is a hydrocarbon.

11. A process for the epoxidation of an olefin comprising contacting said olefin with hydrogen peroxide in the presence of a catalytically effective amount of a catalyst comprising a zeolite having a mole ratio of an oxide selected from silicon oxide, germanium oxide, and mixtures thereof to an oxide selected from titanium oxide and mixtures of titanium oxide with boron oxide, greater than about 20:1, wherein the elemental mole ratio of titanium to silicon, germanium or mixture thereof is at least about 0.005, and wherein the zeolite has the X-ray diffraction lines of Table I.

12. The process of claim 11 wherein the elemental mole ratio of titanium to silicon, germanium or mixture thereof is about 0.005 to about 0.2.

13. The process of claim 11 wherein the elemental mole ratio of titanium to silicon, germanium or mixture thereof is about 0.01 to about 0.05.

* * * * *